United States Patent
El Zoghbi et al.

(10) Patent No.: US 9,452,052 B2
(45) Date of Patent: Sep. 27, 2016

(54) ARTIFICIAL KNEE JOINT

(75) Inventors: Gaser El Zoghbi, Rombach (CH); Ulrich Reinbold, Aarau (CH)

(73) Assignee: Smith and Nephew Orthopaedics AG, Rotkreuz (CH)

( * ) Notice: Subject to any disclaimer, the term of this patent is extended or adjusted under 35 U.S.C. 154(b) by 491 days.

(21) Appl. No.: 13/260,686

(22) PCT Filed: Mar. 27, 2009

(86) PCT No.: PCT/EP2009/053677
§ 371 (c)(1), (2), (4) Date: Jun. 20, 2014

(87) PCT Pub. No.: WO2010/108550
PCT Pub. Date: Sep. 30, 2010

(65) Prior Publication Data
US 2015/0018960 A1    Jan. 15, 2015

(51) Int. Cl.
*A61F 2/38*    (2006.01)
*A61F 2/30*    (2006.01)

(52) U.S. Cl.
CPC .............. *A61F 2/3836* (2013.01); *A61F 2/389* (2013.01); *A61F 2/3859* (2013.01); *A61F 2/3886* (2013.01); *A61F 2002/302* (2013.01); *A61F 2230/0065* (2013.01)

(58) Field of Classification Search
CPC .................................. A61F 2/38; A61F 2/3886
See application file for complete search history.

(56) References Cited

U.S. PATENT DOCUMENTS

| | | | |
|---|---|---|---|
| 6,123,729 A * | 9/2000 | Insall | A61F 2/3859 623/20.31 |
| 2009/0326668 A1* | 12/2009 | Dun | A61F 2/3886 623/20.33 |

* cited by examiner

*Primary Examiner* — Yashita Sharma
*Assistant Examiner* — Daniel Bissing
(74) *Attorney, Agent, or Firm* — Taft Stettinius & Hollister LLP (57) ABSTRACT

An artificial knee joint (1) is described and comprises a femoral component (10) and a tibial component (30), for attachment to the femur (2) and tibia (3) of a patient (4) respectively. The femoral component (10) comprises a lateral condyle (11) and a medial condyle (12) which extend from the posterior (13) to the anterior (14) of the femoral component (10). A femoral gap (15) is provided between the lateral (11) and medial (12) condyles extending from the posterior (13) toward the anterior (14) of the femoral component (10). The lateral (11) and medial (12) condyles are joined at the anterior (13) of the femoral component (10) to form a patella tracking path or bearing surface (16) which is located at and forms the anterior end of the gap (17). A femoral cam (18) is provided bridging the posterior ends of both the lateral (11) and medial (12) condyles, and forms a posterior end of the gap (19), wherein the femoral cam (18) is structured to have the shape of a section of a ring (20). The tibial component (30) is provided with two approximately symmetric articulation bearing surfaces (31, 32) either side of a central post (33), wherein the articulation bearing surfaces (31, 32) are for receiving the lateral (11) and medial (12) condyles of the femoral component (10), and the post (33) is shaped such that it will fit within the femoral gap (15).

18 Claims, 9 Drawing Sheets

ARTIFICIAL KNEE JOINT

This application is a United States National Phase filing of International Application No. PCT/EP2009/053677 filed on Mar. 27, 2009, which is herein incorporated in it's entirety.

BACKGROUND TO THE INVENTION

The present disclosure relates to an artificial knee joint usable for replacement of damaged or worn out knees. In particular, conditions such as arthritis or rheumatism leads to damage to the knee joint, which can be alleviated by replacement with an artificial joint. Likewise, it is clear that people who suffer from accidents can also benefit from such a replacement joint.

It is typical in the art to provide a knee joint comprising two components. The first component is intended to be attached to the femur of a patient, with the second component being attached to the tibia of the patient. A bearing surface is provided between these two components, such that a lower portion of the femoral component lies on an upper portion of the tibial component and can slide thereon. As is clear, the knee joint requires that the tibia and femur rotate and flex with respect to each other, this is normally achieved by having a curved surface on the outer side of the femoral component. Providing this curved bearing surface on the femoral component, allows the femur to rotate and flex over the bearing surface of the tibial component in much the same way as a normal knee joint functions.

Clearly it is necessary to restrict the amount of relative rotation and flexion possible between the femoral and tibial components, which is often achieved by providing a slot or gap in a portion of the femoral component, and an appropriate post on the tibial component.

Positioning the post within the gap, allows the femoral component to move between two set rotation and flexion stops, and can thus be utilised to mirror and duplicate the normal motion of a knee. That is, the post will restrict the motion of the femoral component to the extent of the gap provided in the femoral component, thus allowing the amount of relative rotation and flexion between the two components to be tailored and appropriately limited.

U.S. Pat. No. 5,549,686 describes a replacement knee joint, in which a post interacts with a gap as described above. In order to allow for high degrees of bending of the knee joint, a femoral cam is provided at the rear-most portion of the femoral component. This femoral cam interacts with the posterior side of the post, and thus can be utilised to allow high angles of bend and rotation between the femoral and tibial components.

A structure which is similar to the above prior art is also described in U.S. Pat. No. 6,123,729. This document further discusses the internal socket within the femoral component for interacting with the end of the femur. Again, the curved structure of the outer surface of the femoral component allows for the relative rotation between the femoral and tibial components, and a femoral cam is provided for interacting with a post on the tibial component to improve the high flexion angle between these two components.

One aspect which is not addressed by either of these prior art replacement knees, is the general asymmetry between the numerous tendons and ligaments present within the knee. It is not unusual for the tendons and ligaments of a patient to have different strengths and lengths, which is particularly apparent at high flexion angles of the knee joint. This will tend to try and pull the orientation of the knee joint out of complete alignment, such that a degree of twist occurs between the tibia and femur of the patient, which then gets translated to the knee joint. The present disclosure relates to a solution to this problem and presents a knee joint suitable for allowing the femoral and tibial components to rotate and/or wobble at very high flexion angles, in particular a controlled relative rotation/wobbling motion.

SUMMARY OF THE DISCLOSURE

In order to address the above problem, the present disclosure relates to a replacement or artificial knee joint comprising a tibial and femoral component for attachment to the tibia and femur of a patient, respectively. In particular, these two components are separate, and are respectively attached to the bones of the leg in the patient. The femoral component is preferably comprised of two condyles which extend generally from the anterior to posterior of the component. These condyles, a lateral and medial condyle, are joined at the anterior side and form a patella plate. A gap is provided between the two condyles which extends up to the patella plate in the front anterior direction, and extends to the back of the condyles in the posterior direction. Bridging the posterior end of the two condyles, and forming the end of the gap, is a lateral cam, which serves to control the range of femoral component flexion relative to the tibial component.

The femoral cam of the present disclosure is preferably provided with a structure that is a portion of a ring. In other words, the femoral cam bridging the posterior ends of the two condyles has a curved profile bridging the gap between the two condyles, which further preferably tends to extend slightly higher than the upper ends of each condyle. This section of a ring will generally, but not necessarily, be aligned in a vertical plane which will follow the central axis of the femur when the femoral component is attached thereto. In other words, when looking from the back of the femoral component, the femoral cam is seen as the section of the ring, and extends from the posterior ends of each condyle slightly upward and bridges the two. It is not necessary, however, for the femoral cam to extend higher than the height of the condyles, as long as the profile is that of a ring section.

The tibial component of the artificial knee joint comprises a central post which is intended to be located within the gap of the femoral component. The interaction between the post and gap in the two components will provide and control the range of motion of the knee joint. Either side of this central post the tibial component comprises medial and lateral bearing surfaces, which are preferably symmetrically formed. By having a symmetric structure to the tibial component, only one tibial component need be produced for either a left or right knee replacement. If required, however, it is possible to provide the medial and lateral bearing surfaces with an asymmetric design. Further, these bearing surfaces could be provided by an insert into the tibial component. The bearing surfaces are utilised for receiving the outer condyles of the femoral component, and thus provide the bearing and running surfaces between the femoral and tibial components of the knee joint.

The artificial knee joint may further have a bearing surface provided at the lower posterior end of the post. This articulation bearing surface may be structured to have an indent which matches the outer surface of the femoral cam, such that the femoral cam will snugly fit within this indented articulation surface. At high levels of flexion between the femoral and tibial components, the femoral cam will be received within this high flexion articulation surface or indent, and thus will provide an appropriate bearing between the two components.

In order to allow appropriate rotation and flexion between the femoral and tibial components, the condyles of the femoral component have an outer curved surface. This curved surface will thus allow the appropriate rotation and flexion between the femoral and tibial components. Preferably, the curved surface of the two components has two radii of curvature; a first larger radius of curvature extending from the patella bearing surface toward the posterior of the femoral component. In the region of the condyles next to the lateral cam, a second smaller radius of curvature may be provided, in order to allow high angles of flexion between the two components and further to bring the lateral cam into contact with the high flexion articulation surface.

It is further advantageous if the bearing surfaces provided on the tibial component have an intended curvature which is larger than, approximately the same, or indeed the same, as the first radius of curvature of the condyles. That is, the indent of the bearing surfaces of the tibial component has a radius of curvature which matches the first larger radius of curvature on the femoral component.

When the femoral and tibial components are in contact by means of the first radius of curvature section of the condyles and the bearing surfaces on the tibial component, the two components will be in good mating alignment. Upon rotation and flexion of the femoral component relative to the tibial component, the lateral cam, and more particularly the inner curved surface thereof, will strike the posterior side of the post. At this first point of contact, it is preferable for the lateral cam to be located in the femoral component at a position so as to strike the post at a position part way up the post, and not at the very bottom. When the lateral cam and post first make contact, the lateral cam preferably should not be positioned within the indented high flexion articulation surface. Further, the condyles should preferably be in contact with the bearing surfaces of the tibial portion by means of their first radius of curvature section. That is, the condyles are preferably in contact with the bearing surfaces only at the sections of the first radius of curvature, and not by the sections with the second smaller radius of curvature.

The flexion angle, or angle of rotation, between the femoral and tibial components which has been undertaken to reach the first contact point between the lateral cam and post lies between approximately 55° and 75°. More preferably, this lies between 60° and 70°, and most preferably this lies at 65°. This angle of rotation and flexion is based on the zero point of rotation being the alignment of the femoral and tibial components, such that the leg of the patient would be straight. That is, the two components are aligned such that the femur and tibia of the leg of the patient would be in approximately linear alignment, or put another way the leg of the patient would be at full extension.

If further rotation and flexion of the femoral component with respect to the tibial component is undertaken, the contact point will proceed from the portion of the condyles with a first larger radius of curvature to the portion with the second smaller radius of curvature. This process will tend to bring the lateral cam down the posterior side of the post and into mating alignment with the high flexion articulation surface. That is, the provision of the second lower radius of curvature of the condyles will bring the lateral cam down the posterior side of the shaft, and into the indent of the high flexion articulation surface.

If once more the zero point of rotation and flexion is defined as being the full extension of the patient's leg, i.e. a straight leg, the point at which the femoral cam is in mating agreement with the high flexion articulation surface will occur between approximately 95° and 115°; preferably this occurs between 100° and 110°; most preferably at a rotation and flexion of 105°.

By rotating the femoral component further, the ring-like structure to the lateral cam will tend to lift the femoral component with relation to the tibial component. That is, the ring-like section shape of the lateral cam leads to the femoral component lifting out of contact with the tibial component, to some degree. The femoral component will remain in contact with the tibial component via the lateral cam and indented high flexion articulation surface, but the condyles will rise above the bearing surfaces and will not maintain contact. With the point of contact being solely between the lateral cam and the articulation bearing surface, the femoral component will be allowed to wiggle and rotate in order to bring one of the condyles into contact with the bearing surface. Such a wobble between the femoral and tibial components is a direct result of the ring-like structure to the femoral cam, and is useful for accommodating the different strengths of tendons and ligaments of the human knee.

The amount of wobble can lie anywhere between approximately 1° and 8°, and more preferably between about 2° and 5°. Most preferably, the amount of wobble between the femoral and tibial component is 3°.

When the femoral and tibial components are structured such that they can wobble with respect to each other, the outer radial surface of the lateral cam, or ring-like section thereof, has a different radius of curvature from the portion of the high flexion articulation surface with which it is in contact. In other words, the point of contact between the femoral and tibial components is solely by the femoral cam and high flexion articulation surface, and as the femoral cam has a ring-like structure this can slide around the indented section of the high flexion articulation surface this allows the wobble between the femoral and tibial components. Additionally, it is possible for the outer radial surface of the ring-like femoral cam is slightly different from that of the indent of the high flexion articulation surface, which will then also allow for a wobble to occur between the femoral and tibial components.

It is further possible to provide the femoral cam with two radii of curvature in the cross-sectional direction. That is, the lower inner radial section of the femoral cam has a first lower radius of curvature, at the point in which first contact will be made between the femoral cam and the post. Proceeding around the outer surface of the femoral cam in a radial direction, the radius of curvature changes at the upper side of the femoral cam. The radius of curvature at the upper section of the femoral cam can be larger than that at the lower section, and will tend to make the femoral cam somewhat thicker at this point. As the second larger radius of curvature is provided at the upper end of the femoral cam, this will allow for the wobble and rotation between the femoral and tibial components when they are aligned at high flexion angles. Preferably, the first radius of curvature is preferably between 3 mm to 10 mm, more preferably between 3 mm and 6 mm and even more preferably approximately 3.5 mm; and the second is preferably between 5 mm to 15 mm, more preferably between 5 mm and 10 mm and even more preferably approximately 5.5 mm.

The tibial component has three indented sections therein, the two bearing surfaces and the high flexion articulation surface. Preferably, the lowest point thickness of each of these three surfaces is the same, and further preferably this is between approximately 4 mm and 25 mm, more preferably between 6 mm and 15 mm, and even more preferably it is 6 mm. This is in line with SN EN ISO 21536.

DETAILED DESCRIPTION

Figure 1:
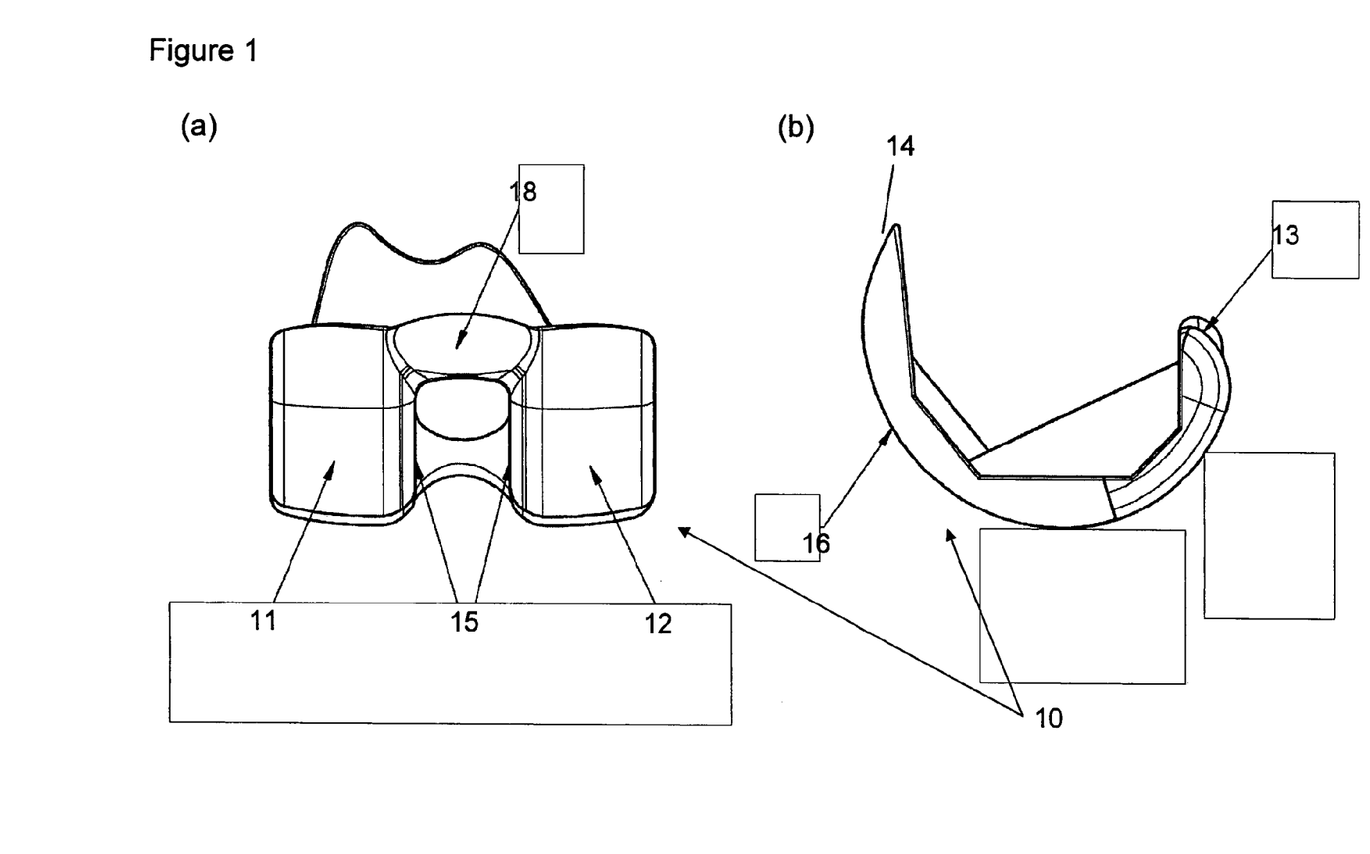
FIG. 1: Two views showing the femoral component of the present disclosure.
Figure 2:
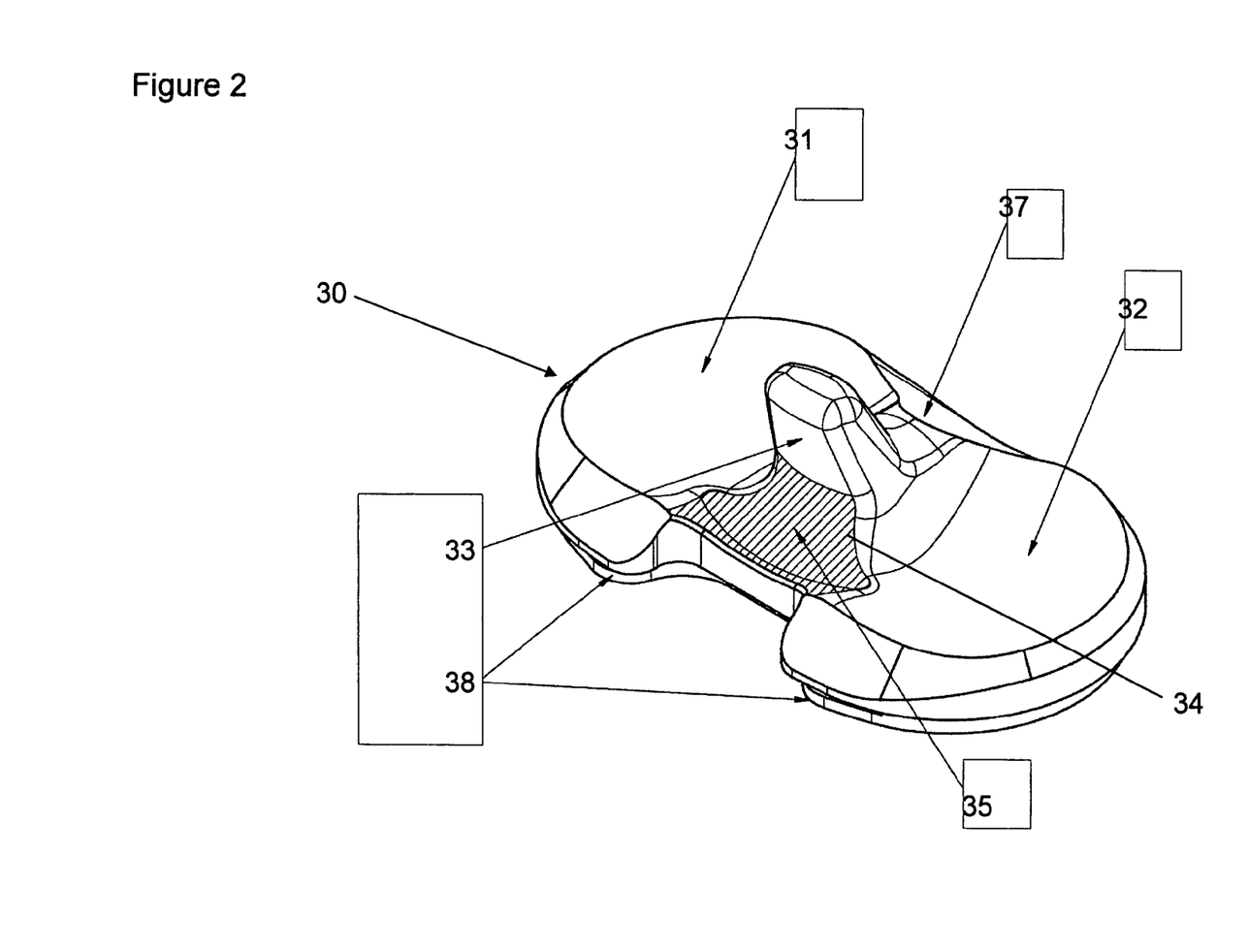
FIG. 2: A perspective view of a bearing inlay or insert for incorporation into the tibial component.
Figure 9:
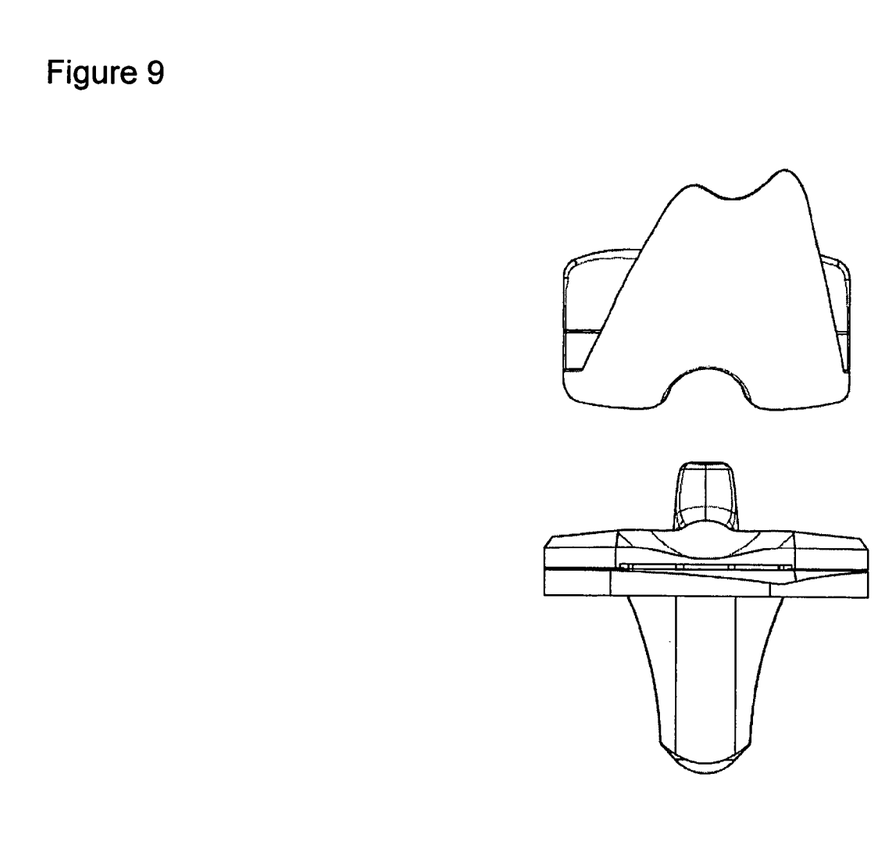
FIG. 9: The femoral and tibial components of the knee joint in alignment.

FIG. 1 shows the femoral 10 component of an artificial knee joint 1; FIG. 2 shows a bearing inlay or insert which can be incorporate within a tibial component 30. As can be seen in FIG. 9, the full tibial component 30 comprises both an upper bearing inlay or insert (which provides the bearing surface over which the femoral component 10 will run) and a lower section which comprises a tibial post for insertion within the tibia 3 of a patient 4. It is possible to provide the tibial component 30 as such a two-piece unit, in which the lower section is perhaps made from a metal and to which the bearing inlay or insert, perhaps formed from polyethylene, is attached. It is further possible to form a combined tibial component 30, comprising both the bearing surface as well as the tibial post as a single unit. For clarity in the following discussion, the term "tibial component 30" is intended to embrace both of these options, and no distinction will be especially made between the bearing inlay or insert as shown in FIG. 2, and the combined option.

As is generally shown in FIGS. 5 to 8, the interaction between the femoral component 10 and tibial component 30 can be seen. In particular, the femoral component 10, as depicted generally in FIG. 1b, is intended to rest on the upper surfaces of the tibial component 30. Further, the lower curved surfaces as seen in FIG. 1b will rest on the upper, generally curved, surfaces of the tibial component 30, as shown in FIG. 2.

The femoral component 10 is intended to be attached to the end of the femur 2 of a patient 4. As will be clear from at least FIG. 1a, the femoral component 10 comprises an interior portion or recess, into which the lower part of the patient's femur 3 is to be inserted and fixed therein. The fixing of a femoral component 10 to the end of the femur 2 is well known, and it is contended that the present knee joint 1, and in particular the femoral component 10 thereof, can be attached to the femur 2 following any of the well known alternatives in the art.

In a similar manner as for the femoral component 10, the tibial component 30 as seen in FIG. 9, is intended to be attached to the upper portion of the tibia 3 of a patient 4. Again, the attachment of such tibial components 30 to the tibia 3 of a patient 4 is well known in the art, and any of the available techniques used for attaching these two items is considered as appropriate for the tibial component 30 of the present disclosure.

As is most clear from FIG. 1, the femoral component 10 of the present disclosure preferably comprises a component with a curved outer surface. This curved outer surface begins at a patella tracking path or bearing surface 16 formed at the anterior 14 of the femoral component 10, and proceeds in a generally posterior direction toward the posterior 13 of the femoral component 10. As can be seen from FIG. 1b, the curved outer and lower surface of the femoral component 10 further preferably has a surface with generally two different radii of curvature. In particular, the outer surface of the femoral component 10 running from the patella bearing surface 16 to the most posterior point of the femoral component 10 has a first radius of curvature. As the outer surface of the femoral component 10 continues, the outer surface generally tends to curve back to progress in the anterior 14 direction, and possesses a second smaller radius of curvature. That is, the outer surface of the femoral component 10 has a tighter curve at its rear-most or posterior 13 side, which curves the posterior 13 end of the femoral component 10 back and over towards the anterior 14 of the femoral component 10.

As can be seen in FIG. 1a, the femoral component 10 comprises two condyles. These two condyles comprise a lateral 11, and medial 12, condyle. Clearly, the femoral component 10 will be structured appropriately for either a left or right femur 3 of a patient 4. In particular, the patella bearing surface 16 will be structured appropriately such that it extends generally toward the lateral side of the femoral component 10, as this will be appropriate for attachment to the femur 2. In the femoral component 10 of the present disclosure, the lateral 11 and medial 12 condyles are separated by a gap 15. This gap 15 is intended to appropriately interact with a post 33 of the tibial component 30. The post 33 of the tibial component 30 can clearly be seen in FIG. 2.

The interaction between the post 33 of the tibial component 30 and the gap 15 of the femoral component 10, is extremely useful for limiting the relative motion of the femoral 10 and tibial 30 components when the knee joint 1 is within the patient 4. As will be discussed in more detail below, the ends of the gap 15 will strike the post 33 during relative rotation of the femoral 10 and tibial 30 components. Clearly, the anterior end 17 of the gap 15 will strike the anterior side 37 of the post 33 in one orientation, and will stop the continued relative rotation of the femoral 10 and tibial 30 components in this direction. Likewise, with relative rotation of the femoral 10 and tibial 30 components in another direction, the posterior end 19 of the gap 15 will strike the posterior side of the post 33, thus tending to stop further rotation of the femoral component 10 with respect to the tibial component 30. As will be seen below, however, the specific structure of the femoral component 10 allows additional rotation of the femoral component 10 to give hyper extension of the knee joint 1.

The anterior end 17 of gap 15 is defined by the patella bearing surface 16 positioned at the anterior ends of the lateral 11 and medial 12 condyles. The posterior end 19 of the gap 15, is provided by a femoral cam 18. As is clear from FIG. 1a the femoral cam 18 is provided as a bridging structure between the lateral 11 and medial 12 condyles. In particular, it will be seen that the upper side of the femoral cam 18 may extend to a higher point than each of the ends of the lateral 11 and medial 12 condyles, although this is not a necessity. This will be discussed in more detail with respect to FIG. 8.

Figure 3:
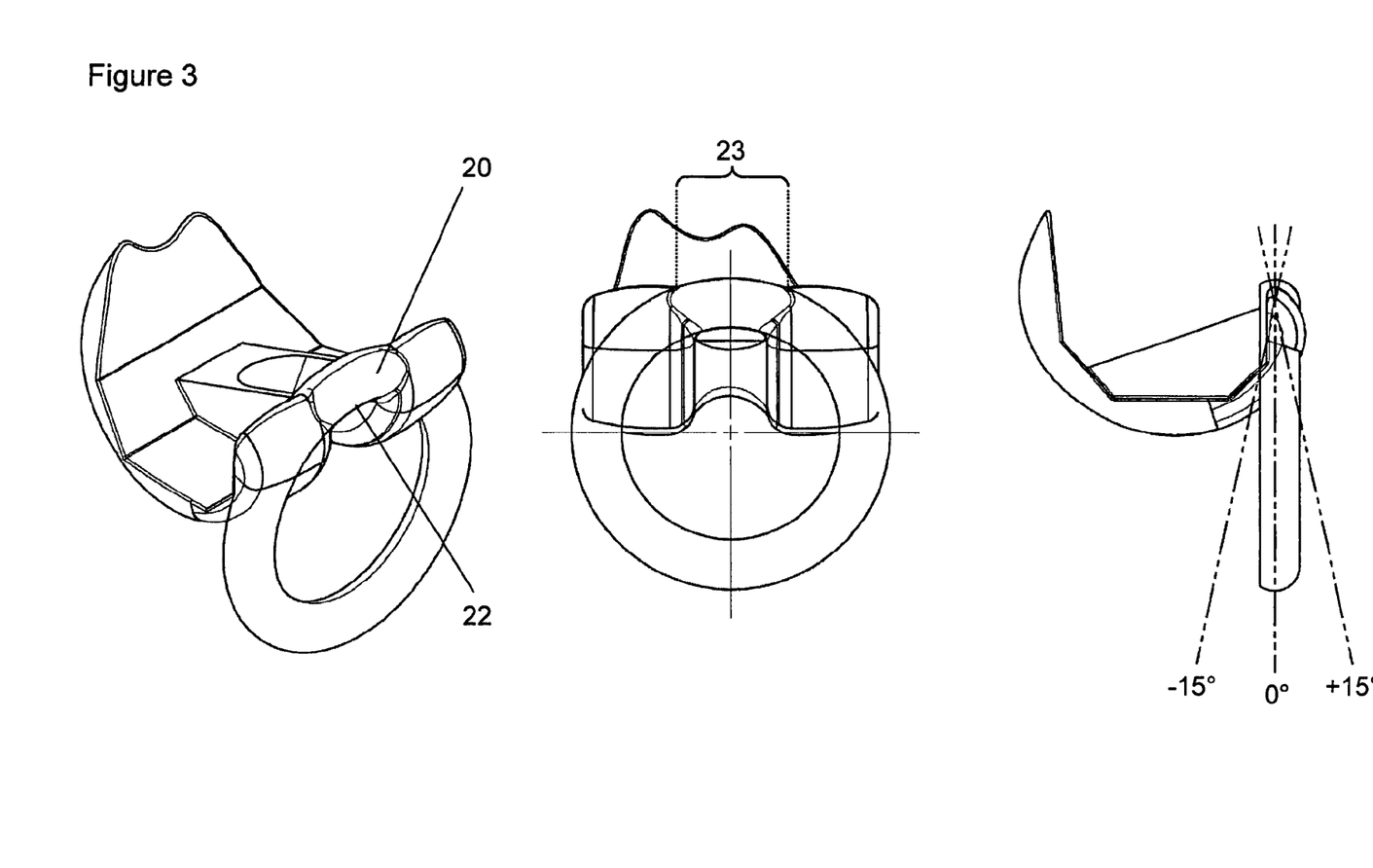
FIG. 3: Views of the femoral component showing the imaginary ring of which the lateral cam provides a section thereof.

In addition to the femoral cam 18 forming a bridge between the lateral 11 and medial 12 condyles, the femoral cam 18 is preferably structured as a section from a ring. This can best be seen in the imaginary views of a ring shown in FIG. 3. As can be seen from FIG. 3, the complete imaginary ring is shown in the diagrams, with the femoral cam 18 being provided by a section thereof. In particular, the ring is sized and positioned such that the section thereof will appropriately bridge the lateral 11 and medial 12 condyles, and may also extend higher than the ends of the lateral 11 and medial 12 condyles, to the same height, or lower. The inner surface of the femoral cam 18, that which is facing the interior recess of the femoral component 10, can be provided with a flat surface, or indeed a curved surface following the general shape of the ring as shown in FIG. 3. The interior portion of the femoral component 10 in general can be formed as a series of straight sided pieces, in order to give appropriate bonding surfaces to the femur 2. Likewise, it is equally possible for the interior surfaces of the femoral component 10 to be given a different structure, as required, for appropriate bonding to the femur 2. For example, instead of having a flat side to the interior portion of the section of the ring 20, the section of the ring 20 could extend in a curved manner into the interior of the femoral component 10, thus forming a section of a torus.

As can be seen in the Figure, the imaginary ring may be provided such that it aligns with the extended leg of the patient 4. As is seen in the figures, the imaginary ring is generally shown such that it extends from the femoral cam 18 straight down. It is not necessary, however, for the ring to extend in this manner, and as can be seen by the lines in FIG. 3, it is also possible for the imaginary ring to generally extend under the femoral component 10. This angle will tend to mean that the femoral cam 18 is curved and moves away from the internal section of the femoral component 10. Clearly, the imaginary ring could extend away from the underside of the femoral component 10, such that the upper portion forming the femoral cam 18 will tend to move into the inner portion of the femoral component 10. If straight down is considered as the 0° point, the offset from this can lie in the range between ±15°, more preferably ±10°, even more preferably ±5°.

The imaginary ring may have an outer radius which lies between 20 mm and 50 mm; preferably the outer radius lies between 25 mm and 45 mm; further preferably the outer radius lies between 30 mm and 40 mm; most preferably the radius is approximately 35 mm. The actual radius of the imaginary ring can be tailored as appropriate for the size of implant. This change in the radius will also lead to an appropriate change in the high flexion articulation surface 35, as introduced below.

It is shown in the figures that the femoral cam 18, and thus the imaginary circle definable by this, lies at 90° from the long axes of each of the lateral 11 and medial 12 condyles. That is, the femoral cam 18 bridges the gap 15 in the shortest way when viewed from the top of the femoral component 10. It is also possible for the femoral cam 18 to bridge the gap 15 differently, such that one end of the femoral cam 18 is slightly further back than the other. That is, one end of the femoral cam 18 is further from the centre of the femoral component 10, most easily seen when viewed from the top down, than the other. This could be useful for specifically introducing a twist into the knee joint 1 at high flexion of the knee, in order to offset some known misalignment in the knee joint 1.

Looking at FIG. 2, we see a perspective view of the tibial component 30. As has already been discussed above, the tibial component 30 may comprise a post 33 which is for interacting with the gap 15 of the femoral component 10. Advantageously, the post 33 and gap 15 are of approximately the same width, thus reducing lateral motion of the femoral 10 tibial 30 component. Likewise, it is equally possible to provide the gap 15 slightly wider than the post 33, thus allowing for a little bit of lateral motion between the femoral 10 and tibial components 30. Indeed, if the lower portion of the post 30 is slightly tapered outward, and the lower portion of the gap 15 has an equal tapering, it is possible to get a preferred mounting position between the femoral 10 and tibial 30 components, whilst also allowing for a desired level of lateral movement (which includes none) between the two components, to accommodate the appropriate stresses and strains placed on the knee joint 1.

As has also been discussed above, as the anterior side 37 of the post 33 will meet the anterior side 17 of gap 15 in order to stop additional rotation between the femoral 10 and tibial components, the post 33 may preferably be formed to be quite wide at its base. This additional thickness at the base of the post 33 will clearly improve the general strength of the post 33 and knee joint 1. Given that the knee joint 1 is intended to rotate in only one orientation from the point where the gap 15 strikes anterior side 37 of the post 33, it is important to provide a thick width to the lower portion of the post 33 in order to ensure the proper action of the knee joint 1.

Either side of the post 33 are lateral 31 and medial 32 articulation bearing surfaces. These two bearing surfaces 31, 32 provide the surfaces on the tibial component 30 upon which the lateral 11 and medial 12 condyles will rest and move. Generally, the surface presented by the articulation bearing surfaces 31, 32 will match the surfaces presented by the lateral 11 and medial 12 condyles. That is, the curve of the articulation bearing surfaces 31, 32 may be larger than, approximately the same, or the same, as the curve on the lateral 11 and medial 12 condyles. This matching of the surfaces will lend stability to the knee joint 1, and will reduce any unwanted relative motion between the femoral 10 and tibial 30 components.

Shown generally at 38 in FIG. 2, the tibial component 30 may be provided with slots, or the like, in order to improve the fixation of the tibial component 30 with the tibia 3. These fixation means 38 can take a variety of forms, and are generally provided to allow for the tibial component 30 to be held within an appropriate portion of the tibia 3. Additional fixation means 30 can also be provided at the anterior side of the tibial component 30, and could include a series of clip-like members in order to aid connection between the tibial component 30 and the tibia 3.

As is clear from the FIG. 2, at the lower posterior end of the post 34, the tibial component 30 may comprise a high flexion articulation surface 35. This high flexion articulation surface 35, is advantageously provided with a generally indented shape 36 which will tend to match external surface 21 of the femoral cam 18. That is, the high flexion articulation surface 35 may be structured to accept the femoral cam 18, shaped with the section of a ring 20. As will again be discussed below, at high levels of flexion of the knee, the femoral cam 18 will be brought into contact with the surface of the high flexion articulation surface 35 if present, and these two will provide a bearing surface there-between at particularly large angles of rotation between the femoral 10 and tibial 30 components, i.e.: high levels of knee flexion. This is a particular result of the external surface of the lateral 11 and medial 12 condyles having the second smaller radius of curvature, i.e. a higher degree of curvature, at the section or portion near the femoral cam 18. This lower radius of curvature will tend to bring the femoral cam 18 into contact with the high flexion articulation surface 35, thus providing the bearing surface at high flexion angles.

Figure 4:
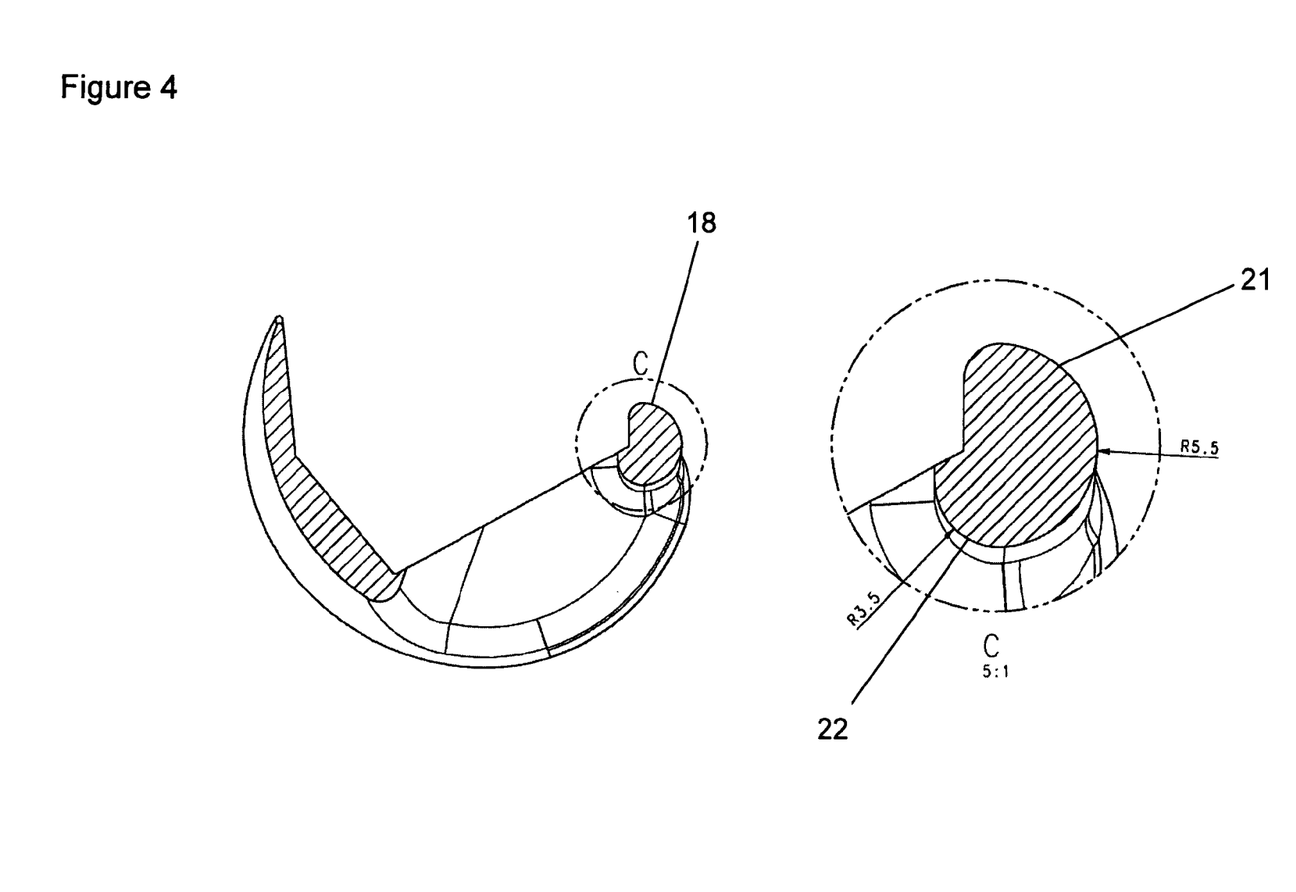
FIG. 4: Cross-section of the femoral component showing the two radii of curvature of the femoral cam.

In addition to the lateral 11 and medial 12 condyles advantageously having a surface comprising approximately two radii of curvature, the femoral cam 18 may also possess two such radii of curvature. This can be seen clearly in FIG. 4. As is shown in this figure, the lower inner surface of the femoral cam 18, that shown as the inner diameter of the ring 22, may generally have a lower radius of curvature than the outer most posterior side of the femoral cam 18. Whilst two radii of curvature are shown in FIG. 4, these are by way of example only, and are not intended to limit the disclosure. Indeed, the radius of curvature of each section of the femoral cam 18 can be chosen appropriately with regard to the size of the knee joint 1. As will be seen below, the lower radius of curvature of the interior side of the femoral cam 18 is advantageous in bringing the femoral cam 18 and high flexion articulation surface 35 into contact.

Figure 5:
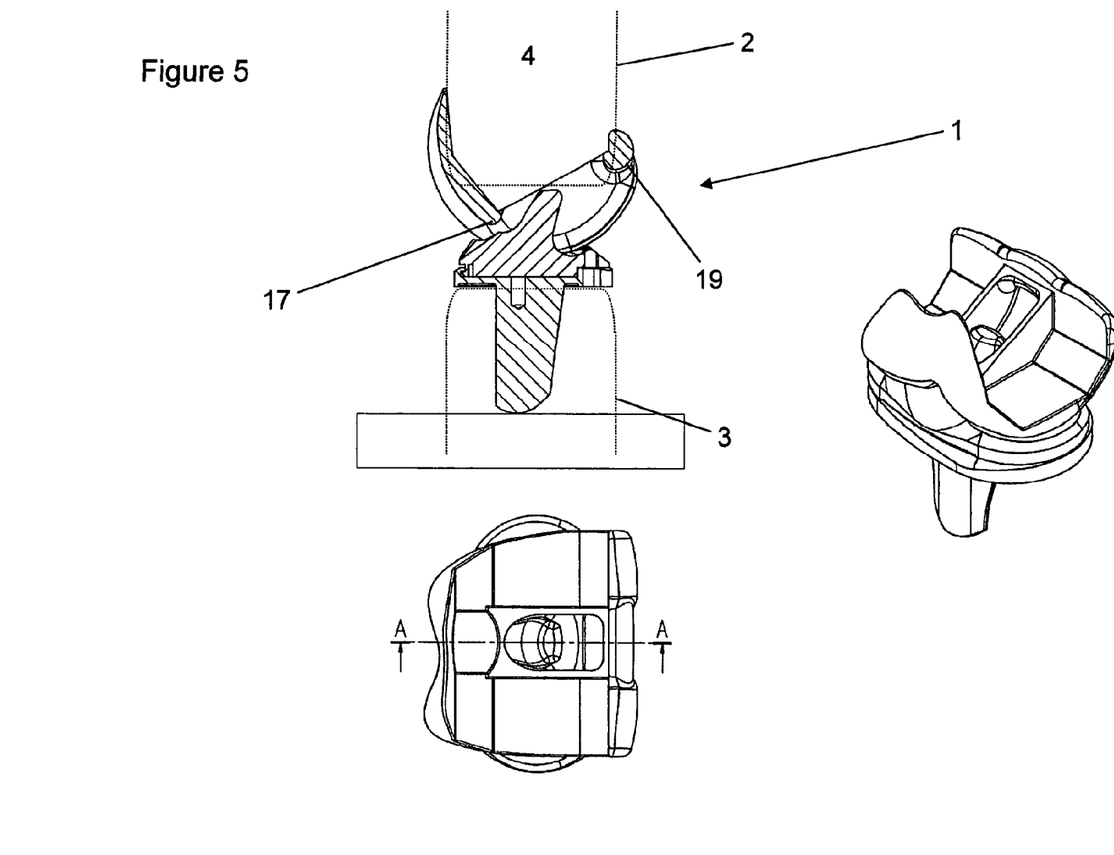
FIG. 5: Femoral and tibial component in alignment at zero point of rotation.

Looking at FIGS. 5 to 8, we see the rotational interaction between the femoral 10 and tibial 30 components. In particular, in FIG. 5 we see the orientation in which the femur 2 and tibia 3 of the leg of the patient 4 would be in alignment, that is the knee is fully extended. In this orientation, and as shown in FIG. 5, the anterior 17 of the gap 15 is not quite in contact with the anterior side 37 of the post 33. The knee joint 1 will need to allow the femur 2 and tibia 3 to be slightly misaligned in a rearward direction, which is essentially the locking of the knee joint in a hyper extended position. That is, it is possible with a normal leg to lock the knee by generally positioning the femur 2 and tibia 3 backwards so that the knee joint is locked, this is hyper extension of the knee. The orientation of the femoral 10 and tibial 30 components shown in FIG. 5, is the complete alignment of femur 2 and tibia 3, or the knee fully extended. As will be appreciated, the slight gap between the anterior 17 of the gap 15 and the anterior side 37 of the post 33, will allow for the knee joint 1 to lock in the way described above for a standard knee. The position of the femoral component 10 with respect to the tibial component 30, such that the femur 2 and tibia 3 are in linear alignment and the knee is in full extension, is considered to be a zero degree rotation point as shown in FIG. 5. That is, for the sake of providing a reference point, the orientation of the femoral 10 and tibial 30 components shown in FIG. 5 is the zero rotation point.

Figure 6:
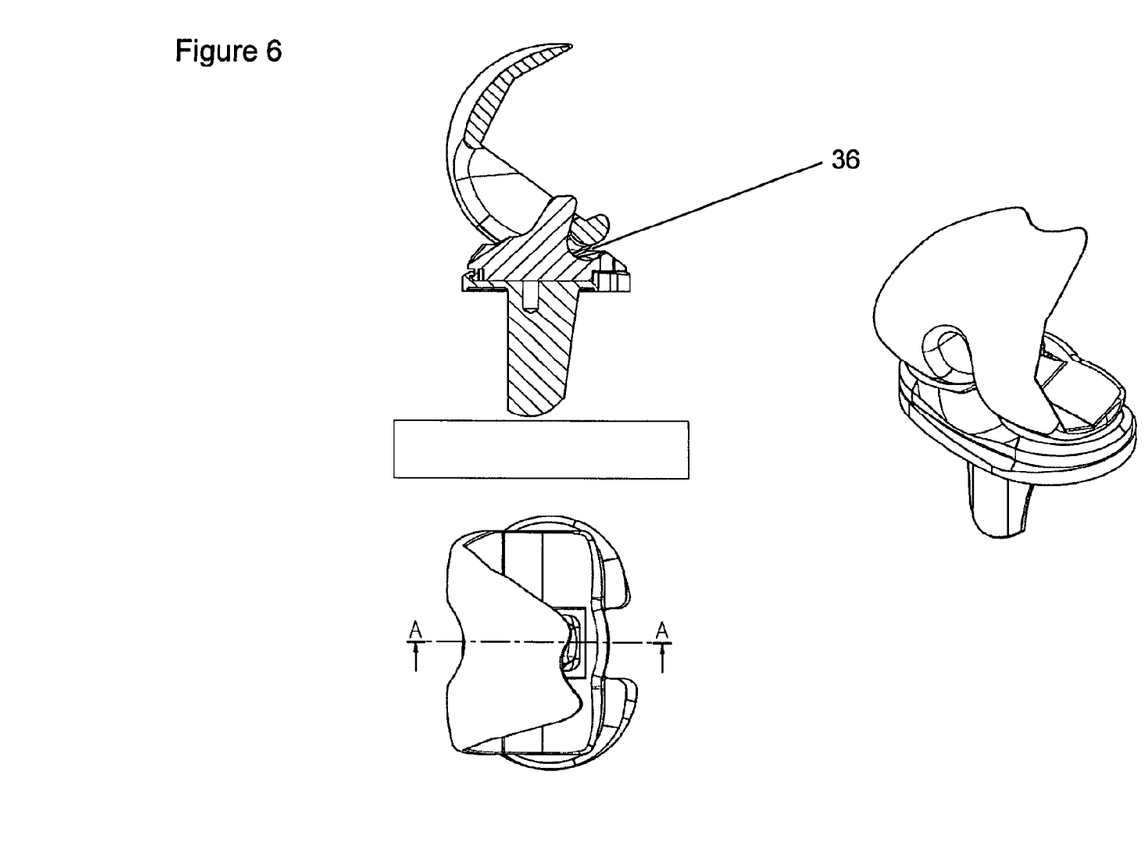
FIG. 6: Femoral and tibial component in alignment with first point of contact between femoral cam and post.

Turning to FIG. 6, we see the orientation in which the femoral component 10 has rotated with respect to the tibial component 30, that is the knee has undergone flexion. During this rotation, the lateral 11 and medial 12 condyles slide over the articulation bearing surfaces 31, 32. If the external surface of the condyles 11, 12 matches the surface of the articulation bearing surfaces 31, 32, this rotation is improved and should proceed in a smooth manner. As will be clear from the figures, at a certain level of rotation, the femoral cam 18 strikes the posterior side of the post 33. As shown in FIG. 6, the amount of rotation which has occurred in FIG. 6, when compared with the zero point shown in FIG. 5, lies between approximately 55° and 75°. More preferably, this level of rotation lies between approximately 60° and 70°. The most preferable amount of rotation of the femoral component 10 with regard to the tibial component 30 (flexion of the knee joint 1) at the point where the femoral cam 18 first strikes the post 33, is 65°. This level of rotation is, once again, measured with respect to the zero point as shown in FIG. 5: that of alignment of the tibia 3 and femur 2 of the patient 4, or full extension of the knee.

It is also important to note that at the position shown in FIG. 6, the lateral 11 and medial 12 condyles are still in good contact with the articulation bearing surfaces 31, 32. That is, preferably the point of contact between the femoral 10 and tibial 30 components is between the lateral 11 and medial 12 condyles across the full surface of the articulation bearing surfaces 31, 32. The femoral component 10 is still in contact with tibial component 30 by means of the first larger radius of curvature of the curved outer surface of the femoral component 10. At the point when the femoral cam 18 strikes the post 33, the contact is preferably still over the full outer curved surface of the femoral component 10 at the first larger radius of curvature.

The structure of the femoral component 10 is such, however, that additional rotation of the femoral component 10 with respect to the tibial component 30 will then proceed by means of the surface with the second lower radius of curvature. In other words, the point at which the femoral cam 18 strikes the posterior side of the post 33, marks the end of the contact between the femoral component 10 and tibial component 30 by means of the curved outer surface of the first larger radius of curvature. With additional rotation, the outer surface of the femoral component 10 will proceed to the second smaller radius of curvature, which will tend to lift the lateral 11 and medial 12 condyles out of contact with the articulation bearing surfaces 31, 32, in the regions of the first larger radius of curvature.

With continued rotation of the femoral component 10 with regard to the tibial component 30 (more knee flexion), i.e. progressing further than as shown in FIG. 6, the surface with the second radius of curvature of the lateral 11 and medial 12 condyles is preferably brought into contact with the articulation bearing surfaces 31, 32. This is as described above. As the rotation continues using the second lower radius of curvature surface, the contact between the femoral cam 18 and posterior side of the post 33 will tend to continue. In particular, the contact point between the femoral cam 18 will move from a position at least some way up the posterior side of the post 33, as shown in FIG. 6, until the entire external surface 21 of the femoral cam 18 is positioned within the indented shape 36 of the high flexion articulation surface 35. This is the exact orientation as shown in FIG. 7.

Figure 7:
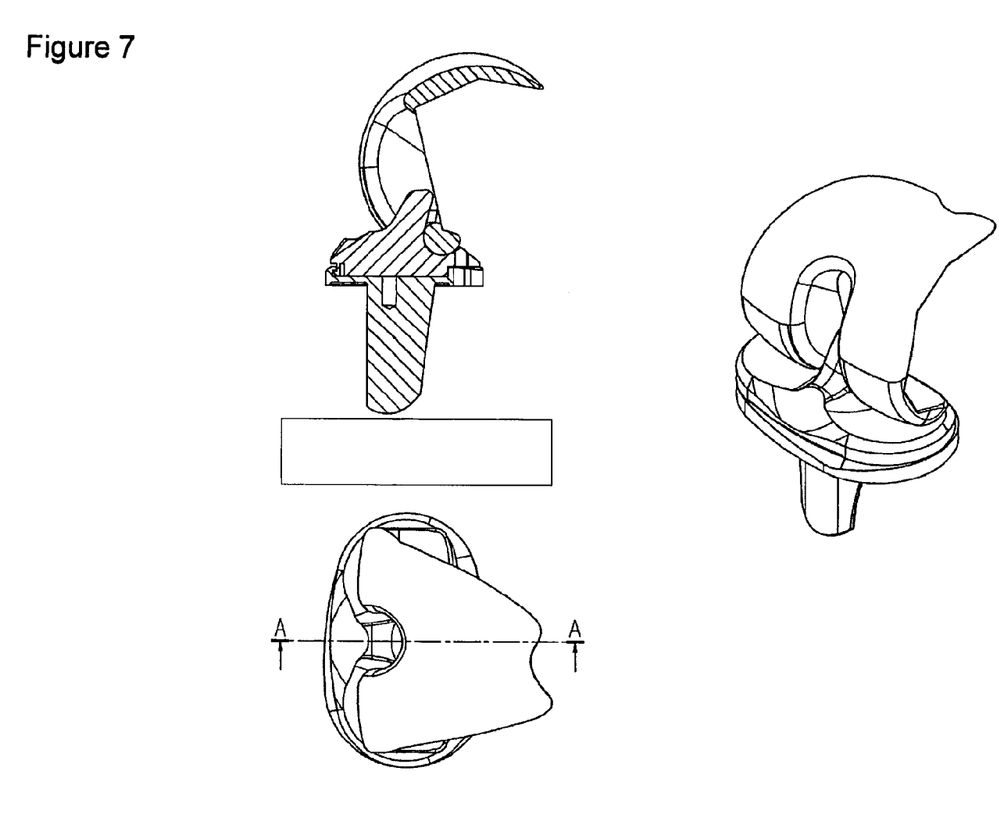
FIG. 7: Femoral component and tibial component at point of first contact between femoral cam and high flexion articulation surface.

Moving from FIGS. 6 to 7 by rotation of the femoral component 10, one may understand that the second lower radius of curvature surface of the lateral 11 and medial 12 condyles, will tend to bring the point of connection between the femoral cam 18 and post 33 lower, also with the aid of the lower radius of curvature surface of the femoral cam 18. That is, the two appropriate surfaces of the condyles 11, 12 and femoral cam 18, are appropriately matched in order to allow the femoral cam 18 to slide down the surface of the post 33 from the initial point of contact part way up the post 33, to the complete interacting contact at the high flexion articulation surface 35. When the femoral cam 18 is positioned in total contact with the high flexion articulation surface 35, the posterior ends of the lateral 11 and medial 12 condyles are still in contact with the articulation bearing surfaces 31, 32. At this point, it is clear that a high level of contact between the femoral 10 and tibial 30 components is still maintained.

The rotation angle as shown in FIG. 7 of the present disclosure lies between 95° and 115°, in particular with respect to the zero point as shown in FIG. 5 and discussed above. Preferably, the angle of rotation as shown in FIG. 7 lies between 100° and 110° from the zero point. Most preferably, the point at which the external surface of the femoral cam 18 is completely in contact with the high flexion articulation surface 35 and the posterior most points of the lateral 11 and medial 12 condyles is still in contact with the articulation bearing surfaces 31, 32, occurs at 105° from the zero point of rotation shown in FIG. 5, that of knee full extension.

If one continues further rotation from the point shown in FIG. 7, toward the deep or high flexion point of the knee joint 1, the lateral 11 and medial 12 condyles will actually be lifted out of contact with the articulation bearing surfaces 31, 32. As has been discussed above, the femoral cam 18 is provided as a section of a ring 20, which tends to lift the femoral cam 18 the lateral 11 and medial 12 condyles out of contact with the articulation bearing surfaces 31, 32. Furthermore, should the upper surface of the femoral cam 18 extend beyond and above the ends of the lateral 11 and medial 12 condyles, this will also aid the break of contact, although this is not a requirement. This removal of contact between the condyles 11, 12 and articulation bearing surfaces 31, 32 is particularly advantageous, as it allows the femoral component 10 to rotate and wobble with respect to the tibial component 30 at high flexion of the knee joint 1. In particular, the rotation of the femoral component 10 can occur around what would be the longitudinal axis of the tibia 3, and also the rotation of the tibial component 30 around what would be the longitudinal axis of the femur 2.

Figure 8:
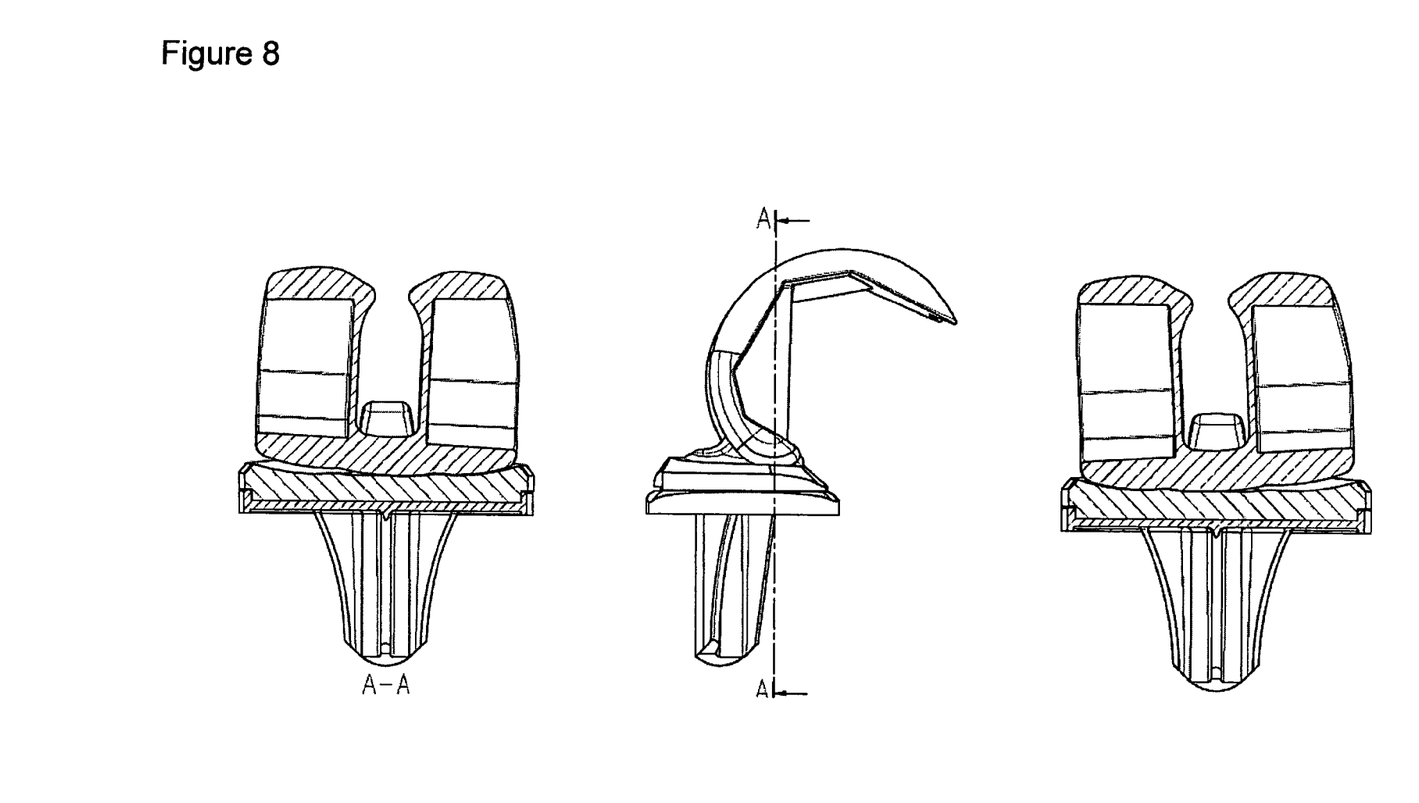
FIG. 8: Femoral and tibial component showing wobble of femoral component with respect to tibial component.

As will be well known to the person skilled in the art, the tendons and ligaments, in particular the patella ligaments and the medial and lateral ligaments, of a patient 4 are generally not identical behind the knee. That is, the tendons and ligaments will tend to pull the knee joint slightly out of alignment at particularly high angles of flexion. In order to allow for the difference between the strengths of the tendons and ligaments behind the knee of the patient 4, the intentional rotation and wobble between the femoral 10 and tibial 30 components will account for such. As will be quite clear, considering the structure of the joint as shown in FIG. 8, the slight rotation and wobble of the femoral component 10 with respect to the tibial component 30 will accommodate any difference in strength between the tendons and ligaments of the knee joint of the patient 4, and will reduce the strain on such tendons and ligaments.

Clearly, the amount of allowable wobble and rotation can be changed merely by changing the external surface 21 of the femoral cam 18, such that the lateral 11 and medial 12 condyles are brought further out of contact with the articulation bearing surfaces 31, 32. An ideal degree of wobble or tilt between the femoral 10 and tibial 30 components is, however, approximately +/−3°, as can be seen between FIGS. 8a and 8c. As has been discussed above, this raising of the femoral component 10 with regard to the tibial component 30 at very high degrees of rotation is a result of the ring-like structure of the femoral cam 18. Providing the outer surface higher than the condyles aids this wobble, but is not essential. Additionally, as the femoral cam 18 will rotate within the high flexion articulation surface 35, a good degree of contact is maintained between the femoral 10 and tibial 30 components, and this proceeds via the femoral cam 18 and matching surface of the high flexion articulation surface 35. Further, as the upper larger radius of curvature surface of the femoral cam 18 has a smooth and generally constant radius of curvature, the amount of lift obtained between the femoral 10 and tibial 30 components can be kept constant, and is tuneable according to the requirements of the individual knee joint 1.

The angle or rotation at which the lift between the lateral 11 and medial 12 condyles and the articulation bearing surfaces 31, 32 occurs, is after the rotation point shown in FIG. 7. That is, depending upon when the femoral cam 18 makes full contact with the high flexion articulation surface 35, additional rotation will move the condyles 11, 12 out of contact with the articulation bearing surfaces 31, 32. As has been described above, a particularly preferred angle of rotation shown in FIG. 7 is 105°. If this degree of rotation is chosen as the desired point at which the femoral cam 18 is brought into contact with the high flexion articulation surface 35, above a rotation of 105° will lead to the condyles 11, 12 being lifted from the articulation bearing surfaces 31, 32. Of course, the point at which the contact is broken can also be chosen by appropriately structuring the femoral cam 18 and high flexion articulation surface 35, and in particular the amount of rotation between the femoral 10 and tibial components 30 which has been undertaken to bring the contact about.

The above disclosure is not intended to comprise preferred or required combinations of features. Indeed, each aspect according to each of the components, femoral 10 and tibial 30, are intended to be viewed more as optional or perhaps advantageous features, but no specific combination should be taken therefrom. The intended scope of protection from the present disclosure is as given in the appended claims.

1 Knee joint
2 Femur
3 Tibia
4 Patient
10 Femoral component
11 Lateral condyle
12 Medial condyle
13 Posterior
14 Anterior
15 Femoral gap
16 Patella tracking path/bearing surface
17 Anterior of gap
18 Femoral cam
19 Posterior end of femoral gap
20 Section of a ring
21 External surface of (18)
22 Inner diameter of the ring
23 Outer radial surface of the ring
30 Tibial component
31 Articulation bearing surface - LAT
32 Articulation bearing surface - MED
33 Post
34 Lower posterior end of post
35 High flexion articulation surface
36 Indented shape of 35
37 Anterior side of post
38 Fixation means

What is claimed is:

1. An artificial knee joint comprising a femoral component and a tibial component, for attachment to a femur and tibia of a patient respectively; wherein the femoral component having a lateral condyle and a medial condyle extending from a posterior to an anterior of the femoral component and wherein a femoral gap is provided between the lateral and medial condyles extending from the posterior toward the anterior of the femoral component, wherein further the lateral and medial condyles are joined at the anterior of the femoral component to form a patella tracking path or bearing surface which is located at and forms an anterior end of the gap;

a femoral cam bridging the posterior ends of both the lateral and medial condyles and forming a posterior end of the femoral gap, wherein the femoral cam is structured to have a shape of a section of a ring, the femoral cam including a first portion and a second portion, the first portion having a first radius of curvature, the second portion having a second radius of curvature that is different than the first radius of curvature; and the tibial component is provided with two approximately symmetric articulation bearing surfaces and a high flexion articulation surface, the two approximately symmetric articulating bearing surfaces positioned on either side of a central post, wherein the articulation bearing surfaces are for receiving the lateral and medial condyles of the femoral component, and the central post is shaped such that it will fit within the femoral gap, the high flexion articulation surface having an indented shape inwardly extending at a lower posterior end of the central post into a portion of the tibial component, the first portion of the femoral cam sized to contact the central post at a position remote from the high flexion articulation surface at least when the femoral component is at a first angular position relative to the tibial component, the second portion of the femoral cam sized to contact the high flexion articulation surface at least when the femoral component is at a second angular position relative to the tibial component, the indented shape of the high flexion articulation surface being shaped to matingly engage the second radius of curvature of the second portion of the femoral cam.

2. The artificial knee joint of claim 1, wherein an outer surface of the lateral and medial condyles has a curved surface which has a first condyle radius of curvature which is approximately constant from the patella tracking path or bearing surface to the posterior of the femoral component, and which has a second condyle radius of curvature at a portion near the femoral cam, wherein the first condyle radius of curvature is larger than the second condyles radius of curvature.

3. The artificial knee joint of claim 2, wherein the articulation bearing surfaces have indented surfaces which have a bearing radius of curvature larger than the first condyle radius of curvature of the lateral and medial condyles.

4. The artificial knee joint of claim 2, wherein the outer surface of the lateral and medial condyles having the first condyle radius of curvature is positioned on the femoral component to contact the articulation bearing surfaces of the tibial component when the femoral and tibial components are at the first angular position, the central post being positioned to extend through the femoral gap when the femoral and tibial components are at the first angular position, and further wherein the femoral cam is sized not to contact the high flexion articulation surface when the femoral and tibial components are at the first angular position.

5. The artificial knee joint of claim 4, wherein the outer surface of the lateral and medial condyles having the second condyle radius of curvature is positioned on the femoral component to contact the articulation bearing surfaces of the tibial component when the femoral and tibial components are at the second angular position.

6. The artificial knee joint of claim 4, wherein if a zero rotation point is defined as being when the lateral and medial condyles are in contact with the articulation bearing surfaces and the femoral and tibial components are oriented such that the femur and tibia of a patient would be in approximately linear alignment such that the knee would be in full extension, an amount of rotation which the femoral component has undergone at the point as defined in claim 5, occurs between 55° and 75°.

7. The artificial knee joint of claim 4, wherein the femoral component is structured to contact the high flexion articulation surface when the second angular position is between 95° and 115° relative to a zero rotation point, the zero rotation point being a relative position at which the lateral and medial condyles contact the articulation bearing surfaces and the femoral and tibial components are oriented such that the femur and tibia of a patient would be in approximately linear alignment such that the knee would be in full extension.

8. The artificial knee joint of claim 4, wherein the femoral component is structured to only contact the tibial component via contact between the femoral cam and the high flexion articulation surface when the femoral component is at an angular position relative to a zero rotation point that is greater than 90°, the zero rotation point being a relative position at which the lateral and medial condyles contact the articulation bearing surfaces and the femoral and tibial components are oriented such that the femur and tibia of a patient would be in approximately linear alignment such that the knee would be in full extension.

9. The artificial knee joint of claim 8, wherein as the femoral cam is structured as a section of a ring when the femoral and tibial components are contacted only via the femoral cam and the high flexion articulation surface, the femoral cam is able to wobble in the lateral and medial directions before the posterior ends of either the lateral or medial condyles is brought into contact with the respective articulation bearing surface.

10. The artificial knee joint of claim 9, wherein this amount of wobble is between about 1° and 8°.

11. The artificial knee joint of claim 1, wherein the first radius of curvature of the femoral cam is at an upper, outer diameter of the ring and posterior sections, and the second radius of curvature is at a lower and inner diameter of the section of the ring, wherein the first radius of curvature is between 5 mm to 15 mm and the second radius of curvature is between 3 mm to 10 mm.

12. The artificial knee joint of claim 1, wherein a minimum thickness of both the articulation bearing surfaces and the high flexion articulation surface of the tibial component are approximately the same, and further this thickness lies between 4 mm and 25 mm.

13. The artificial knee joint of claim 1, wherein an imaginary ring can be drawn which completes the section of the ring forming the femoral cam, and this imaginary ring has an outer radius which lies between 20 mm and 50 mm; and the imaginary ring is structured so that it extends downward from the posterior of the femoral gap so that it would be directly in line with tibia of a patient, if a 0° reference line is defined as exactly in line with the tibia, the imaginary ring can lie at an angle which is in the range between ±15° from this reference line.

14. An artificial knee joint comprising:

a femoral component having a lateral condyle and a medial condyle extending from a posterior to an anterior of the femoral component, the lateral condyle and a medial condyle having a first curved surface having a first condyle radius and a second curved surface having a second, different condyle radius;

a femoral gap positioned between the lateral and medial condyles, the femoral gap extending from the posterior toward the anterior of the femoral component, the lateral and medial condyles being joined at the anterior of the femoral component to form a bearing surface, the bearing surface forming an anterior end of the gap;

a femoral cam bridging the posterior ends of both the lateral and medial condyles and forming a posterior end of the femoral gap, the femoral cam having a shape of a section of a ring, the femoral cam including a first portion and a second portion, the first portion having a first radius of curvature, the second portion having a second radius of curvature that is different than the first radius of curvature; and a tibial component having a first articulation bearing surface, a second articulation bearing surface, a central post, and a high flexion articulation surface, the central post shaped to fit within the femoral gap, the high flexion articulation surface having an indented shape inwardly extending at a lower posterior end of the central post into a portion of the tibial component, the first portion of the femoral cam sized to contact the central post at a position remote from the high flexion articulation surface at least when the first curved surface of the lateral and medial condyles contacts the first and second articulation bearing surface, the second portion of the femoral cam sized to contact the high flexion articulation surface at least when the second curved surface of the lateral and medial condyles contacts the first and second articulation bearing surface, the second radius of curvature of the femoral cam having a different radius of curvature than a radius of curvature of the high flexion articulation surface, and wherein differences between the second radius of curvature of the femoral cam and the radius of curvature of the high flexion articulation surface accommodates wobble between with respect to the tibial and femoral components at high levels of rotation.

15. An artificial knee joint for attachment to the fervor and tibia of a patient, comprising a femoral component having a lateral condyle and a medial condyle extending from a posterior to an anterior of the femoral component such that a femoral gap is provided between the lateral and medial condyles extending from the posterior toward the anterior of the femoral component, wherein the lateral and medial condyles are joined at the anterior of the femoral component to form a patella bearing surface which is located at and forms an anterior end of the gap;

a femoral cam bridging the posterior ends of both the lateral and medial condyles and forming a posterior end of the femoral gap, wherein the femoral cam is structured to have the shape of a section of a ring, the femoral cam including a first portion and a second portion, the first portion having a first radius of curvature, the second portion having a second radius of curvature that is different than the first radius of curvature; and a tibial component having two approximately symmetric articulation bearing surfaces and a high flexion articulation surface, the two approximately symmetric articulating bearing surfaces positioned on either side of a central post, wherein the articulation bearing surfaces are structured to receive the lateral and medial condyles of the femoral component, and the central post is shaped to fit within the femoral gap, the high flexion articulation surface having an indented shape inwardly extending at a lower posterior end of the central post into a portion of the tibial component, the first portion of the femoral cam sized to contact the central post at a position remote from the high flexion articulation surface at least when the femoral component is at a first angular position relative to the tibial component, the second portion of the femoral cam sized to contact the high flexion articulation surface at least when the femoral component is at a second angular position relative to the tibial component, the first angular position being different than the second angular position, the indented shape of the high flexion articulation surface being shaped to mate the second radius of curvature of the second portion of the femoral cam.

16. The artificial knee joint of claim 15, wherein an outer surface of the lateral and medial condyles has a curved surface which has a first condyle radius of curvature which is approximately constant from the patella bearing surface to the posterior of the femoral component, and which has a second condyle radius of curvature at the portion near the femoral cam, wherein the first condyle radius of curvature is larger than the second condyle radius of curvature.

17. The artificial knee joint of claim 16, wherein the articulation bearing surfaces have indented surfaces having a bearing radius of curvature at least approximately equal to the first condyle radius of curvature of the lateral and medial condyles.

18. The artificial knee joint of claim 17, wherein the first portion of the femoral cam is sized to contact the central post, but not contact the high flexion articulation surface, when the first condyle radius of curvature of the outer surface of the lateral and medial condyles contact the bearing surface, and further wherein the second portion is sized to matingly engage the indented shape of the high flexion articulation surface when the second condyle radius of curvature of the outer surface of the lateral and medial condyles contact the bearing surface.

* * * * *